United States Patent
Yu et al.

(10) Patent No.: US 10,758,625 B2
(45) Date of Patent: Sep. 1, 2020

(54) BISPECIFIC ANTIBODY CAPABLE OF BEING COMBINED WITH IMMUNE CELLS TO ENHANCE TUMOR KILLING CAPABILITY, AND PREPARATION METHOD THEREFOR AND APPLICATION THEREOF

(71) Applicant: BENHEALTH BIOPHARMACEUTIC (SHENZHEN) CO., LTD., Shenzhen (CN)

(72) Inventors: Haoyang Yu, Shenzhen (CN); Zhengcheng Li, Shenzhen (CN); Jing Su, Shenzhen (CN)

(73) Assignee: BENHEALTH BIOPHARMACEUTIC (SHENZHEN) CO., LTD., Shenzhen (CN)

( * ) Notice: Subject to any disclaimer, the term of this patent is extended or adjusted under 35 U.S.C. 154(b) by 328 days.

(21) Appl. No.: 15/548,630

(22) PCT Filed: Apr. 14, 2016

(86) PCT No.: PCT/CN2016/079307
§ 371 (c)(1),
(2) Date: Aug. 3, 2017

(87) PCT Pub. No.: WO2016/165632
PCT Pub. Date: Oct. 20, 2016

(65) Prior Publication Data
US 2018/0021440 A1  Jan. 25, 2018

(30) Foreign Application Priority Data
Apr. 14, 2015  (CN) .......................... 2015 1 0175130

(51) Int. Cl.
*A61K 47/59* (2017.01)
*A61K 39/44* (2006.01)
(Continued)

(52) U.S. Cl.
CPC ............ *A61K 47/593* (2017.08); *A61K 39/44* (2013.01); *A61K 47/6849* (2017.08);
(Continued)

(58) Field of Classification Search
None
See application file for complete search history.

(56) References Cited

U.S. PATENT DOCUMENTS

2004/0219203 A1   11/2004   Griffiths et al.

FOREIGN PATENT DOCUMENTS

CN   104271602 A   1/2015
CN   104829730 A   8/2015
(Continued)

OTHER PUBLICATIONS

Dominguez et al., Vaccine 28 (2010) 1383-1390 (Year: 2010).*
(Continued)

*Primary Examiner* — Karl J Puttlitz
(74) *Attorney, Agent, or Firm* — Scully Scott Murphy & Presser

(57) ABSTRACT

The present invention provides a bispecific antibody capable of being combined with immune cells to enhance a targeting tumor killing capability, and a preparation method therefor and an application thereof. Antibodies and degradable nanoparticles are connected by using a chemical method, so as to make the one nanoparticle be connected to two or more antibody molecules at the same time, wherein one antibody can be specifically bound with immune cells, and the other antibody or the other antibodies can be specifically bound to
(Continued)

tumor cells so as to achieve the effect of enhancing the capability of the immune cells for specifically killing tumor cells in a targeting way.

6 Claims, 10 Drawing Sheets

(51) Int. Cl.
  *A61K 47/68* (2017.01)
  *C07K 16/30* (2006.01)
  *A61K 47/69* (2017.01)
  *C07K 16/28* (2006.01)
  *C07K 16/32* (2006.01)
  *A61K 39/00* (2006.01)

(52) U.S. Cl.
  CPC ...... *A61K 47/6851* (2017.08); *A61K 47/6935* (2017.08); *A61K 47/6937* (2017.08); *C07K 16/2803* (2013.01); *C07K 16/2809* (2013.01); *C07K 16/2815* (2013.01); *C07K 16/2887* (2013.01); *C07K 16/3069* (2013.01); *C07K 16/3092* (2013.01); *C07K 16/32* (2013.01); *A61K 2039/505* (2013.01); *A61K 2039/507* (2013.01); *C07K 2317/31* (2013.01); *C07K 2317/73* (2013.01)

(56) References Cited

FOREIGN PATENT DOCUMENTS

| WO | WO 2004/110390 A2 | 12/2004 |
| WO | WO 2005/103081 A2 | 11/2005 |
| WO | 2014/153002 A1 | 9/2014 |
| WO | 2017/219974 A1 | 12/2017 |

OTHER PUBLICATIONS

Kodama et al., Cancer Immunol Immunother (2001) 50: 539-548 (Year: 2001).*

Zhi L. et al., "Cytotoxicity of Cytokine-Induced Killer Cells Targeted by the Bispecific Antibody Anti-CD3xanti-AFP on AFP Positive Hepatoma Cells", Chinese Journal of Biochemical Pharmaceutics, pp. 297-301 (May 31, 2010), together with an English-language abstract.

Tang, PhD J. et al., "Bispecific Antibodies, Nanoparticles and Cells: Bringing the Right Cells to Get the Job Done", Expert Opin Biol Ther. 15(9):1251-1255 (2015).

International Search Report dated Jul. 21, 2016 issued in PCT/CN2016/079307.

Li, Zhengcheng et al., "Production and function evaluation of a kind of bispecific antibody crosslinked with PLGA nanoparticles in vitro", Immunological Journal (Jan. 2016), vol. 32 No. 1, pp. 34-37, with English translation.

Cheng K. et al., "Magnetic Antibody-Linked Nanomatchmakers for Therapeutic Cell Targeting", Nature Communications 5:4880 (Sep. 10, 2014).

Dominguez A L et al., "Targeting the Tumor Microenvironment With Anti-Neu/Anti-CD40 Conjugated Nanoparticles for the Induction of Antitumor Immune Responses", Vaccine 28:1383-1390 (Feb. 3, 2010).

Katayose Y. et al., "MUC1-Specific Targeting Immunotherapy With Bispecific Antibodies: Inhibition of Xenografted Human Bile Duct Carcinoma Growth", Cancer Research 56:4205-4212 (Sep. 15, 1996).

Mahapatro A. et al., "Biodegradable Nanoparticles are Excellent Vehicle for Site Directed In-Vivo Delivery of Drugs and Vaccines", Journal of Nanobiotechnology 9(1):55 (Jan. 1, 2011).

Takemura S-I et al., "A Mutated Superantigen SEA D227A Fusion Diabody Specific to MUC1 and CD3 in Targeted Cancer Immunotherapy for Bile Duct Carcinoma", Cancer Immunol Immunother 51(1):33-44 (Mar. 1, 2002).

Yeheskely-Hayon D. et al., "Optically Induced Cell Fusion Using Bispecific Nanoparticles", Small 9 (22):3771-3777 (Nov. 25, 2013).

European Supplementary Partial Search Report dated Aug. 1, 2018 received in European Patent Application No. 16 77 9607.

Glorius, P. et al., "The novel tribody [(CD20)2 x CD16] efficiently triggers effector cell-mediated lysis of malignant B cells", Leukemia, vol. 27, No. 1, pp. 190-201 (Jun. 4, 2012).

Kellner, C. et al., Heterodimeric bispecific antibody-derivatives against CD19 and CD16 induce effective antibody-dependent cellular cytotoxicity against B-lymphoid tumor cells, Cancer Letters, vol. 303, No. 2, pp. 128-139 (Apr. 28, 2011).

Schlenzka, J. et al., "Combined effect of recombinant CD19 x CD16 diabody and thalidomide in a preclinical model of human B cell lymphoma", Anti-Cancer Drugs, vol. 15, pp. 915-919 (Oct. 2014).

Extended Supplementary Partial European Search Report dated Nov. 26, 2019 received in European Patent Application No. 16 90 0170.8.

* cited by examiner

BISPECIFIC ANTIBODY CAPABLE OF BEING COMBINED WITH IMMUNE CELLS TO ENHANCE TUMOR KILLING CAPABILITY, AND PREPARATION METHOD THEREFOR AND APPLICATION THEREOF

TECHNICAL FIELD

The present invention relates to the field of immunotherapy, and particularly to a bispecific antibody capable of being combined with immune cells to enhance a targeting tumor killing capability, and a preparation method therefor and an application thereof.

BACKGROUND ART

In 2008, New England Journal of Medicine reported that one case of immunotherapy on advanced melanoma was successful, and the patient had developed multiple metastases in the body, all of which disappeared after autologous CD4+T cell treatment, with 26 months of long-term survival via a follow-up. In 2010, FDA approved autologous immune cell therapy technology of Dendreon Corporation for the clinical application of prostate cancer, and in 2011, three scientists engaged in cancer immunotherapy also was awarded Nobel Prize for medicine, suggesting a broad prospect of immunotherapy in malignant treatment.

In recent years, the use of genetically modified and induced T cell immunotherapy has achieved good results on tumor, which points out a new direction for developing immune cell therapy of tumor. This suggests a broad prospect of immunotherapy in malignant treatment.

The immune cell therapy technology has undergone the development of LAK, CIK, DC-CIK and now is rapidly growing toward antigen-loading DC-induced T-cell (DiKat), genetically modified DC-induced T cells (AV/LV-DC-CTL) and genetically modified chimeric antigen receptor T cells (CAR-T). Currently, Novartis announced a result of B lymphoma clinical trial for the CD19 target with a rate of complete efficacy of 93%, further highlighting the prospect of the immune cell therapy of cancer. However, CAR-T is challenged because of its complex cell preparation process, as well as high costs (the cost of each course is expected to be 500,000 US dollars), and currently shows a good efficacy only for CD19-positive B lymphoma, suggesting its obvious limitations.

An urgent need exists for solving the problem on how to develop an immune cell therapy technology, which has enhanced specificity and effectiveness and the advantages of simple and convenient use etc.

Contents of Invention

The present invention provides a bispecific antibody, as well as a preparation method therefor and an application thereof, and particularly a bispecific antibody capable of being combined with immune cells to enhance a targeting tumor killing capability, as well as a preparation method therefor and an application thereof.

To this end, the present invention adopts the following technical solutions:

In a first aspect, the present invention provides a bispecific antibody capable of being combined with immune cells to enhance a targeting tumor killing capability, said bispecific antibody comprising a first antibody moiety that binds to an antigen expressed on an effector T cell and a second antibody moiety that binds to an antigen expressed on a target cell.

The second antibody moiety described herein may be one or more antibodies that can bind to the target cell.

In the present invention, the first antibody moiety and the second antibody moiety are connected by a nanomaterial. The connection can be made by using the carboxyl group of the nanoparticle surface and the amino group of the antibody.

A "multispecific antibody" is an antibody that may simultaneously bind to at least two targets with different structures (e.g., two different antigens, two different epitopes on the same antigen, or a hapten and/or antigen or epitope). A "bispecific antibody" is an antibody that can bind to two targets with different structures simultaneously. The "multispecific antibody" or "bispecific antibody" described herein includes multiple or two antibodies (e.g., two monoclonal antibodies) that are connected by a nanomaterial and bind to different targets. The multispecific antibody or bispecific antibody described herein may have at least one antibody that specifically binds to a T cell and at least one antibody that specifically binds to an antigen produced by a diseased cell, tissue, organ or pathogen, or an antigen related thereto (e.g., a tumor-associated antigen), which antibodies are connected by a nanomaterial.

For the purpose of immune cell targeting therapy, the present invention utilizes the specific binding ability of an antibody to attach the antibodies capable of specifically recognizing a tumor cell and a tumor killer cell to a clinically available degradable nanomaterial, so as to form a bispecific antibody. In contrast, most anti-cancer monoclonal antibodies as a drug for the treatment of diseases are mainly based on their inherent biological functions, including complement-mediated cytotoxicity (CDC), antibody-dependent cell-mediated cytotoxicity (ADCC), apoptosis induction, opsonophagocytosis etc. The bispecific antibody of the invention not only specifically recognizes and binds to a tumor cell, but also recognizes and binds to a killer T lymphocyte, thereby assisting the T cell to recognize the tumor cell and narrowing the physical distance between the tumor cell and the killer T lymphocyte, and thus facilitating the killing of the tumor cell by the T lymphocyte. Accordingly, the specificity and effectiveness of immune cell therapy are strengthened.

The nanomaterial described herein is a biodegradable nanomaterial.

The nanomaterial described herein is generally present in the form of nanoparticle, which is selected from a conventional degradable nanomaterial, such as any of polylactic acid-glycolic acid, polylactic acid, polycaprolactone, polybutylene glycol succinate, polyaniline, polycarbonate, glycolide-lactide copolymer or glycolide-caprolactone copolymer, or a mixture thereof, preferably, but not limited to these.

The nanomaterial used herein possesses the advantages of slow releasing and good biocompatibility etc. For example, PLGA is a pharmaceutical excipient approved by FDA, which has good biocompatibility and biodegradability, no toxicity and irritation, high strength and is easily processed and molded. It is finally decomposed into hydrated carbon dioxide by enzymatically hydrolysis in vivo, and can be completely absorbed within 3-6 months after being implanted into the body.

In the present invention, the target cell is B cell, cancer cell, or pathogen cell, etc.

Preferably, the antigen expressed on the target cell is any one of carbonic anhydrase IX, alpha-fetoprotein, alpha-actinin-4, A3, A33 antibody-specific antigen, ANG2, ART-4, B7, Ba 733, BAGE, BrE3-antigen, CA125, CAMEL, CAP-1, CASP-8/m, CCCL19, CCCL21, CD1, CD1a, CD2, CD3, CD4, CD5, CD8, CD11A, CD14, CD15, CD16, CD18, CD19, CD20, CD21, CD22, CD23, CD25, CD29, CD30, CD32b, CD33, CD37, CD38, CD40, CD40L, CD45, CD46, CD52, CD54, CD55, CD59, CD64, CD66a-e, CD67, CD70, CD70L, CD74, CD79a, CD79b, CD80, CD83, CD95, CD126, CD132, CD133, CD138, CD147, CD154, CDC27, CDK-4/m, CDKN2A, CS1, CXCR4, CXCR7, CXCL12, HIF-1alpha, colon-specific antigen-p (CSAp), CEA (CEACAM5), CEACAM6, c-met, DAM, EGFR, EGFRvIII, EGP-1, EGP-2, ELF2-M, Ep-CAM, Flt-1, Flt-3, folate receptor, G250 antigen, GAGE, gp100, GPA33, GROB, HLA-DR, HM1.24, human chorionic gonadotropin (HCG) and its subunit, HER2/neu, HER3, HMGB-1, hypoxia-inducible factor (HIF-1), HSP70-2M, HST-2, Ia, IGF-1R, IFN-γ, IFN-α, IFN-β, IL-2, IL-4R, IL-6R, IL-13R, IL-15R, IL-17R, IL-18R, IL-6, IL-8, IL-12, IL-15, IL-17, IL-18, IL-23, IL-25, IL-33, insulin-like growth factor-1 (IGF-1), KC4-antigen, KS-1-antigen, KS1-4, L1CAM, Le-Y, LDR/FUT, macrophage migration inhibitory factor (MIF), MAGE, MAGE-3, MART-1, MART-2, NY-ESO-1, TRAG-3, mCRP, MCP-1, MICA, MICB, MIP-1A, MIP-1B, MIF, MUC1, MUC2, MUC3, MUC4, MUC5ac, MUC13, MUC16, MUM-1/2, MUM-3, NCA66, NCA95, NCA90, pancreatic cancer mucin, placental growth factor, p53, PLAGL2, prostate acid phosphatase, PSA, PRAME, PSMA, PlGF, ILGF, ILGF-1R, IL-6, IL-25, ROR-1, RS5, RANTES, T101, SAGE, S100, survivin, survivin-2B, TAC, TAG-72, tenascin, TRAIL receptor, TNF-alpha, Tn antigen, Thomson-Friedrich antigen, tumor necrosis antigen, TROP-2, VEGFA, VEGFR, ED-B fibronectin, WT-1, 17-1A-antigen, complement factor C3, C3a, C3b, C5a, C5, angiogenesis marker, bc1-2, bc1-6, Kras, cMET, oncogene product, HIV virus, *Mycobacterium tuberculosis*, *Streptococcus agalactiae*, meticillin-resistant *Staphylococcus aureus*, *Legionella pneumophila*, *Streptococcus pyogenes*, *Escherichia coli*, *Neisseria gonorrhoeae*, *Neisseria meningitidis*, *Pneumococcus*, *Cryptococcus neoformans*, *Histoplasma capsulatum*, *Hemophilis influenzae* B, *Treponema pallidum*, Lyme disease spirochetes, *Pseudomonas aeruginosa*, *Mycobacterium leprae*, *Brucella abortus*, Rabies virus, Influenza virus, Cytomegalovirus, Type I herpes simplex virus, type II herpes simplex virus, human serum parvo-like virus, respiratory syncytial virus, varicella-zoster virus, hepatitis B virus, hepatitis C virus, measles virus, adenovirus, human T cell leukemia virus, Epstein-Barr virus, murine leukemia virus, mumps virus, vesicular stomatitis virus, Sindbis virus, lymphocyte choriomeningitis virus, Wart virus, Blue tongue virus, Sendai virus, Cat leukemia virus, Reovirus, Poliovirus, Simian virus 40, mouse mammary tumor virus, Dengue fever virus, rubella virus, West Nile virus, *Plasmodium falciparum*, *Plasmodium vivax*, *Toxoplasma gondii*, *Trypanosoma rangeli*, *Trypanosoma cruzi*, *Trypanosoma rhodesiensei*, *Trypanosoma brucei*, *Schistosoma mansoni*, *Schistosoma japonicum*, *Babesia bovis*, *Elmeria tenella*, *Onchocerca volvulus*, *Leishmania tropica*, *Trichinella spiralis*, *Theileria parva*, *Taenia hydatigena*, *Taenia ovis*, *Taenia saginata*, *Echinococcus granulosus*, *Mesocestoides corti*, *Mycoplasma arthritidis*, *M. hyorhinis*, *M. orale*, *M. arginini*, *Acholeplasma laidlawii*, *M. salivarium* and *M. pneumoniae*, preferably any one of CD19, CD20, CD22, CD30, CD33, CD38, CD123, Muc1, Muc16, HER2, HERS, EGFRvIII, VEGFA, CEA, GPA33, GP100, ANG2, L1CAM, ROR-1, CS1, MICA or MICB.

Preferably, the antigen expressed on the effector T cell is any one of ADAM17, CD2, CD3, CD4, CD5, CD6, CD8, CD11a, CD11b, CD14, CD16, CD16b, CD25, CD28, CD30, CD32a, CD40, CD40L, CD44, CD45, CD56, CD57, CD64, CD69, CD74, CD89, CD90, CD137, CD177, CEACAM6, CEACAM8, HLA-DRa chain, KIR, LSECtin or SLC44A2, preferably any one of CD2, CD3, CD4, CD5, CD6, CD8, CD25, CD28, CD30, CD40, CD40L, CD44, CD45, CD69 or CD90.

In a second aspect, the present invention also provides a method of producing a bispecific antibody as described in the first aspect of the invention comprising connecting the nanomaterial to the first antibody moiety and the second antibody moiety.

The method for producing a bispecific antibody according to the present invention comprises the steps of:

(1) preparation, collection and activation of a nanomaterial;

(2) connecting the nanomaterial obtained in step (1) with a mixture of the first antibody moiety and the second antibody moiety.

In the step (1) of the invention, the preparation of the nanomaterial comprises: dissolving the nanomaterial completely by a solvent, stirring and adding water to form a uniform emulsion.

Preferably, the nanomaterial is any one of polylactic acid-glycolic acid, polylactic acid, polycaprolactone, polybutylene glycol succinate, polyaniline, polycarbonate, glycolide-lactide copolymer or glycolide-caprolactone copolymer, or a mixture thereof.

Preferably, the solvent is any one of acetone, butanone, methanol, ethanol or isopropanol, or a mixture thereof.

Preferably, the collection of the nanomaterial comprises: collecting the prepared nanomaterial by centrifugation, and then washing the nanomaterial by resuspending in deionized water twice.

Preferably, the activation of the nanomaterial comprises: activating the nanomaterial for 0.5-5 hours by using a mixed solvent of 1-10 mg/mL 1-ethyl-(3-dimethylaminopropyl) carbodiimide hydrochloride (EDS) and N-hydroxysuccinimide (NHS) at room temperature.

In the step (2) of the invention, the connection comprises: collecting the activated nanomaterial by centrifugation, and then washing the nanomaterial once with the connecting reaction solution, adding a mixture of the first antibody moiety and the second antibody moiety to be connected in an equal volume into the connecting reaction solution, and then resuspending the nanomaterial with the connecting reaction solution containing the first antibody moiety and the second antibody moiety and conducting the connecting reaction for 0.5-5 hours at room temperature. After the reaction, the nanomaterial is collected by centrifugation. The nanomaterial is washed twice in Dulbecco's phosphate buffer saline (D-PBS), and then resuspended in D-PBS and stored at 4° C.

The method for producing bispecific antibodies described herein comprises the following steps:

(1) Preparation of nanomaterials: The nanomaterial is completely dissolved in acetone at a concentration of 5 to 30 mg/mL, and the solution of the nanomaterial with acetone is added to the deionized water in 1:4 v/v of acetone and deionized water with magnetic stirred at 500 to 1500 rpm/min, to form a uniform emulsion and then continue to stir until the volatilization of acetone;

(2) Collection of nanomaterials: collecting the prepared nanomaterials by centrifugation at 8000-15000 rpm/min, and then washing the nanomaterials by resuspending in deionized water twice;

(3) Activation of nanomaterials: activating the nanomaterials by using a mixed solvent of 1-10 mg/mL 1-ethyl-(3- dimethylaminopropyl)carbodiimide hydrochloride and N-hydroxysuccinimide at room temperature for 0.5-5 hours;

(4) Connection of nanomaterials with antibodies: collecting the activated nanomaterials by centrifugation, and then washing the nanomaterials once with 0.1 M D-PBS at pH=8.0, and adding a mixture of the first antibody moiety and the second antibody moiety to be connected in an equal volume into the connecting reaction solution, and then resuspending the nanomaterials with the connecting reaction solution containing the first antibody moiety and the second antibody moiety and conducting the connecting reaction for 0.5-5 hours at room temperature. After the reaction, the nanomaterials are collected by centrifugation. The nanomaterials are washed twice in D-PBS, and then resuspended in D-PBS and stored at 4° C.

In a third aspect, the present invention also provides the use of the bispecific antibody as described in the first aspect in the manufacture of a medicament for the treatment, prevention or diagnosis of a tumor. The tumor includes, but not limited to, liver cancer, non-small cell lung cancer, small cell lung cancer, adrenocortical carcinoma, acute (chronic B) lymphocytoma, myeloma, prostate cancer, breast cancer, esophageal cancer, gastric cancer, colorectal cancer, cervical cancer, kidney cancer, bladder cancer and lymphoma.

In a fourth aspect, the present invention also provides the bispecific antibody according to any one of claims 1 to 3 for use in the treatment or prevention of a tumor. The tumor includes, but not limited to, liver cancer, non-small cell lung cancer, small cell lung cancer, adrenocortical carcinoma, acute (chronic B) lymphocytoma, myeloma, prostate cancer, breast cancer, esophageal cancer, gastric cancer, colorectal cancer, cervical cancer, kidney cancer, bladder cancer and lymphoma.

In a fifth aspect, the present invention provides a method of treating a tumor comprising administering to a subject the bispecific antibody of the invention. The tumor includes, but not limited to, liver cancer, non-small cell lung cancer, small cell lung cancer, adrenocortical carcinoma, acute (chronic B) lymphocytoma, myeloma, prostate cancer, breast cancer, esophageal cancer, gastric cancer, colorectal cancer, cervical cancer, kidney cancer, bladder cancer and lymphoma.

Compared with the prior art, the invention has at least the following beneficial effects:

(1) The bispecific antibody according to present invention can be more quickly, simply and practically produced as compared to the existing bispecific antibodies which are expressed by biological methods. The bispecific antibody according to present invention can be connected directly to the monoclonal antibodies approved on the market. Because the raw materials to be used are all clinically approved on the market, the bispecific antibody prepared according to the invention can quickly enter clinical use;

(2) Compared with immune cell therapy via the genetically-modified chimeric antigen receptor T cell (CAR-T), the bispecific antibody of the present invention has disadvantages such as biodegradability, no gene recombination, low side effect, high safety, low cost, capability to combine respective specific antibodies for various tumor cells, ease of use, etc. According to present invention, a similar effect on targeting and efficiently killing cancer cells can be achieved by administrating the bispecific antibody preparation of the present invention to a subject while returning the CTL cells induced in vitro to the subject via infusion. The resulted side effects are lower than CAR-T therapy;

(3) All of the materials of the present invention can be degraded into non-toxic and harmless products in the human body and can be degraded and metabolized shortly. Accordingly, the present invention is safer than CAR-T.

Specific Mode for Carrying Out the Invention

The invention is described in details through the Examples, with reference to the accompanying drawings.

EXAMPLES

Example 1

Figure 1:
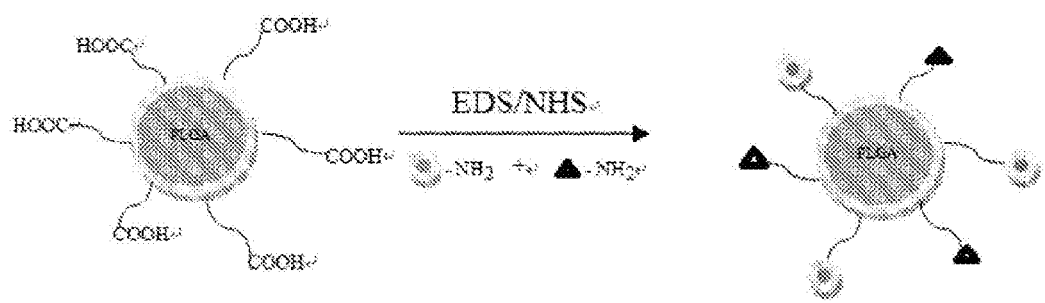
FIG. 1 shows assembling of the bispecific antibody of Example 1.

FIG. 1 shows assembling of the bispecific antibody of this Example. The process comprises the following specific steps:

(1) Preparation of PLGA nanoparticles: PLGA was completely dissolved to a concentration of 5 mg/mL using acetone, and the solution of PLGA and acetone was added into deionized water in a volume ratio of 1:4 of acetone and deionized water with magnetic stirring at 1000 rpm/min, to form a uniform emulsion, and then continue to stir until volatilization of acetone;

(2) Collection of PLGA nanoparticles: collecting the prepared nanoparticles with larger particle size by centrifugation at 8000 rpm/min for 10 min; then collecting the prepared nanoparticles with smaller particle size by centrifugation at 15000 rpm/min for 10 min, and then resuspended in deionized water respectively, and repeatedly washing the nanomaterials twice; nanoparticles with larger particle size and nanoparticles with smaller particle size were carried out as follows;

(3) Activation of PLGA nanoparticles: using a mixed solvent of 5 mg/mL 1-ethyl-(3-dimethylaminopropyl)carbodiimide hydrochloride and N-hydroxysuccinimide at room temperature to activate PLGA nanopoarticles for 1 h;

(4) Connecting PLGA nanoparticles to antibodies: collecting the activated nanomaterials by centrifugation, and then washing the nanomaterial once with 0.1 M D-PBS at pH=8.0, and adding a mixture of CD3 and Muc1 monoclonal antibodies to be connected in an equal volume into the connecting reaction solution, and then resuspending the nanomaterial with the connecting reaction solution containing the first antibody moiety and the second antibody moiety and conducting the connecting reaction for 0.5h at room temperature. After the reaction, the nanomaterial is collected by centrifugation. The nanomaterial is washed twice in D-PBS, and then resuspended in D-PBS and stored at 4° C.

Example 2

The bispecific antibody of Example 1 was added to T cell and cancer cell MCF-7 killing experimental system to detect the ability of the bispecific antibody to enhance the ability of T cell to kill cancer cell, in which T cell: MCF-7=4:1, the reaction time is 8h, in which the control group is the same amount of nanoparticles (not connected to any antibody).

The results are expressed as the average±standard deviation of three independent experiments. The evaluation results are shown in FIG. 2, in which * indicates a significant difference in T test.

Figure 2:
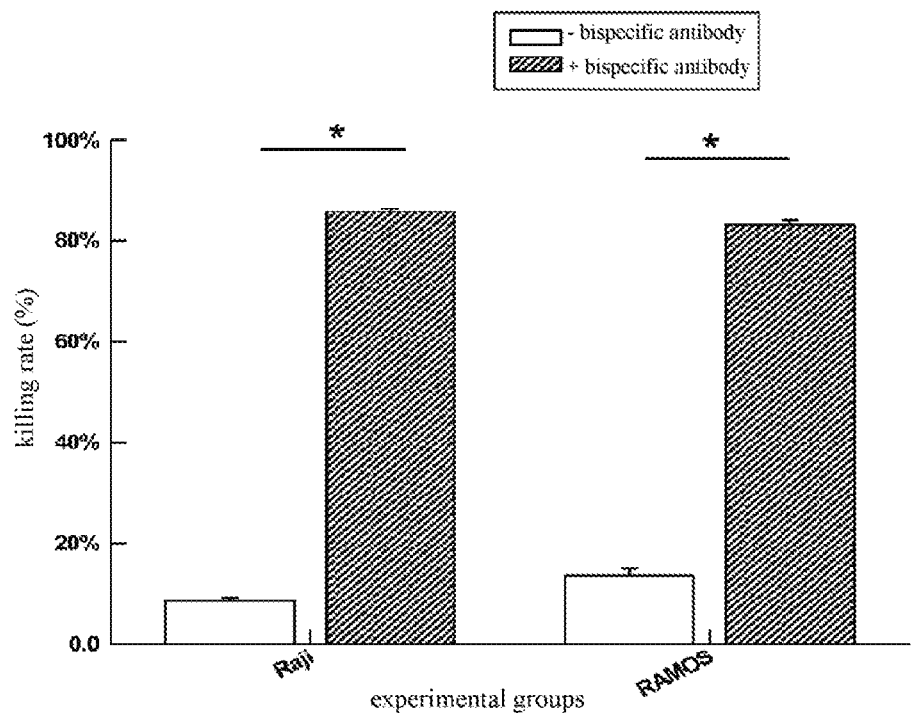
FIG. 2 shows the result of the cell killing experiments of the bispecific antibody of Example 1.

The A in FIG. 2 represents bispecific antibodies connected to nanoparticles with a larger particle size (i.e., particles collected by centrifugation at 8000 rpm/min for 10 min), while B represents bispecific antibodies connected to nanoparticles with a smaller particle size (i.e., particles not collected by centrifugation at 8000 rpm/min for 10 min but collected by centrifugation at 15,000 rpm/min for 10 min).

It can be seen from FIG. 2 that the killing rate of the control group is 7.9%; the killing rate of the group of the bispecific antibodies connected to nanoparticles with a larger particle size is 24.5%; the killing rate of the group of the bispecific antibodies connected to nanoparticles with a smaller particle size is 40.7%.

Example 3

Using PLA as nanomaterial, bispecific antibodies capable of being combined with immune cells to enhance the targeting tumor killing ability were prepared. The preparation process is as follows:

(1) Preparation of PLA nanoparticles: PLA was completely dissolved to a concentration of 15 mg/mL using acetone, and the solution of PLA and acetone was added into deionized water in a volume ratio of 1:4 of acetone and deionized water with magnetic stirring at 500 rpm/min, to form a uniform emulsion, and then continue to stir until volatilization of acetone;

(2) Collection of PLA nanoparticles: collecting the prepared nanoparticles by centrifugation at 8000 rpm/min, and then resuspended in deionized water, and repeatedly washing the nanomaterials twice;

(3) Activation of PLA nanoparticles: using a mixed solvent of 1 mg/mL 1-ethyl-(3-dimethylaminopropyl)carbodiimide hydrochloride and N-hydroxysuccinimide at room temperature to activate PLA nanopoarticles for 0.5h;

(4) Connecting PLA nanoparticles to antibodies: collecting the activated nanomaterials by centrifugation, and then washing the nanomaterials once with 0.1 M D-PBS at pH=8.0, and adding a mixture of CD3 and CD19 monoclonal antibodies to be connected in an equal volume into the connecting reaction solution, and then resuspending the nanomaterials with the connecting reaction solution containing the first antibody moiety and the second antibody moiety and conducting the connecting reaction for 5h at room temperature. After the reaction, the nanomaterials are collected by centrifugation. The nanomaterials are washed twice in D-PBS, and then resuspended in D-PBS and stored at 4° C.

Example 4

Using PCL as nanomaterials, bispecific antibodies capable of being combined with immune cells to enhance the targeting tumor killing ability was prepared. The preparation process is as follows:

(1) Preparation of PCL nanoparticles: PCL was completely dissolved to a concentration of 30 mg/mL using acetone, and the solution of PCL and acetone was added into deionized water in a volume ratio of 1:4 of acetone and deionized water with magnetic stirring at 1500 rpm/min, to form a uniform emulsion, and then continue to stir until volatilization of acetone;

(2) Collection of PCL nanoparticles: collecting the prepared nanoparticles by centrifugation at 15000 rpm/min, and then resuspended in deionized water, and repeatedly washing the nanomaterials twice;

(3) Activation of PCL nanoparticles: using a mixed solvent of 10 mg/mL 1-ethyl-(3-dimethylaminopropyl)carbodiimide hydrochloride and N-hydroxysuccinimide at room temperature to activate PCL nanopoarticles for 5h;

(4) Connecting PCL nanoparticles to antibodies: collecting the activated nanomaterials by centrifugation, and then washing the nanomaterials once with 0.1 M D-PBS at pH=8.0, and adding a mixture of CD3 and CD20 monoclonal antibodies to be connected in an equal volume into the connecting reaction solution, and then resuspending the nanomaterials with the connecting reaction solution containing the first antibody moiety and the second antibody moiety and conducting the connecting reaction for 2.5h at room temperature. After the reaction, the nanomaterials are collected by centrifugation. The nanomaterials are washed twice in D-PBS, and then resuspended in D-PBS and stored at 4° C.

Example 5

The ability of PLGA-connected anti-CD3 and anti-MUC1 bispecific antibodies (anti-CD3-PLGA-anti-MUC1) to kill other tumor cells was evaluated.

Specifically, 5000 target cells were cultured in each well for 12 h in 96-well plates and then the original medium was discarded. The density of DC-CIK cells was adjusted by X-vivo 15 medium without cytokine, resulting in that DC-CIK cell number in a volume of 100 μl was 4 times larger than the target cells (effect-target ratio is 4:1). 100 μl suspension of DC-CIK cells was added in a cancer cell culture plate, and 10 μl prepared bispecific antibody (bispecific antibody preparation content: 0.2 mg, with a total amount of monoclonal antibodies 0.2 μg) was added, incubated for 8 h in an incubator, and then CCK-8 reagent was added, incubated according to the reagent instructions. The absorbance at 450 nm was measured using a microplate reader. Statistical analysis of the data was performed, according to the following formula to calculate killing rate of DC-CIK cells on cancer cells.

Killing rate=[1−(experimental group−effect control group)/(target control group−blank control group)]×100%

The blank control group represents the added medium; the target control group represents the added target cell+medium; the effect control group represents the added the effector cell+medium; the experimental group represents the effector cell+target cell+medium+bispecific antibody.

Figure 3:
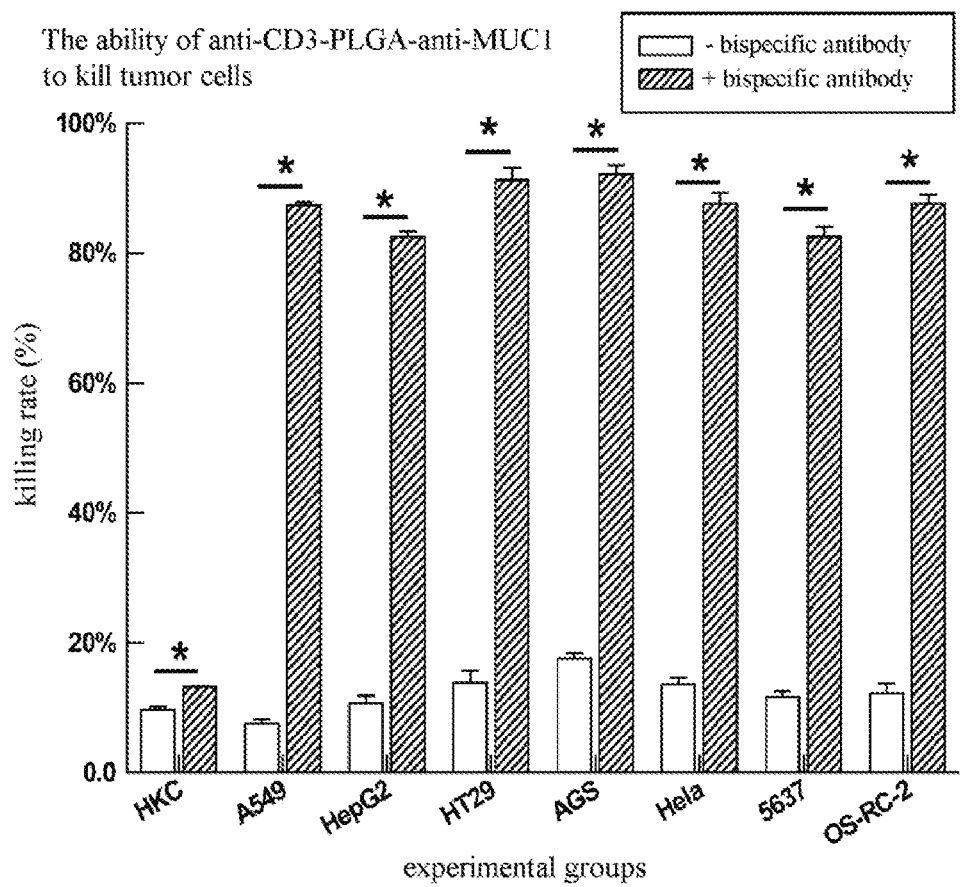
FIGS. 3-9 show the ability of other bispecific antibodies to kill tumor cells.

The results are shown in Table 1 and FIG. 3.

TABLE 1

The ability of anti-CD3-PLGA-anti-MUC1 to kill tumor cells

| Cancer cell | Killing rate | |
| --- | --- | --- |
| | Effect control group | Experimental group |
| HKC | 9.66% | 13.21% |
| A549 | 7.59% | 87.35% |

TABLE 1-continued

The ability of anti-CD3-PLGA-anti-MUC1 to kill tumor cells

| Cancer cell | Killing rate | |
| --- | --- | --- |
| | Effect control group | Experimental group |
| HepG2 | 10.67% | 82.44% |
| HT29 | 13.84% | 91.27% |
| AGS | 17.56% | 92.17% |
| Hela | 13.57% | 87.54% |
| 5637 | 11.64% | 82.51% |
| OS-RC-2 | 12.24% | 87.57% |

Note:
HKC - human embryo kidney epithelial cells;
A549 - human non-small cell lung cancer cells;
HepG2 - human liver cancer cells;
HT29 - human colon cancer cells;
AGS - human gastric adenocarcinoma cells;
Hela - human cervical cancer cells;
5637 - human bladder cancer cells;
OS-RC-2 - human kidney cancer cells.

Example 6

Using the processes method as described above, with PLGA, PLA or PCL as nanomaterials, anti-CD3 and anti-CD33 bispecific antibodies connected via nanoparticles, i.e. anti-CD3-PLGA-anti-CD33, anti-CD3-PLA-anti-CD33 and anti-CD3-PCL-anti-CD33, were prepared. The ability of the bispecific antibodies of the invention to kill tumor cells was evaluated according to the method described in Example 5.

Figure 4:
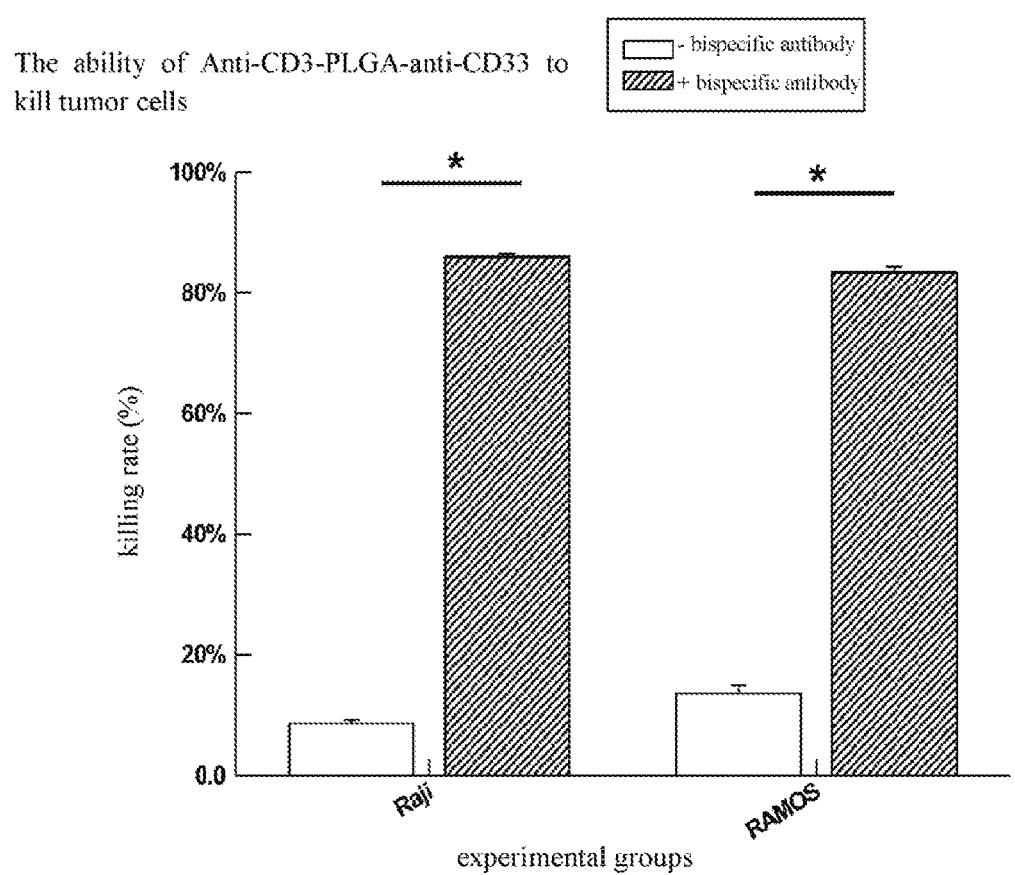

The results are shown in Table 2 and FIG. 4.

TABLE 2

The ability of anti-CD3-PLGA-anti-CD33 to kill tumor cells

| Cancer cell | Killing rate | |
| --- | --- | --- |
| | Effect control group | Experimental group |
| Raji | 8.59% | 85.91% |
| RAMOS | 13.67% | 83.36% |

Note:
Raji - black Burkitt lymphoma cells;
RAMOS - human B lymphocytoma cells.

The bispecific antibodies CD3-PLA-CD33 and CD3-PCL-CD33 both showed a killing rate of more than 83% for black Burkitt lymphoma cells and human B lymphocytoma cells.

Example 6

Using the similar processes as described above, with PLGA, PLA or PCL as nanomaterials, anti-CD8 and anti-MUC1 bispecific antibodies connected via nanoparticles, i.e. anti-CD8-PLGA-anti-MUC1, anti-CD8-PLA-anti-MUC1 and anti-CD8-PCL-anti-MUC1, were prepared. The ability of the bispecific antibodies of the invention to kill tumor cells was evaluated according to the method described in Example 5.

Figure 5:
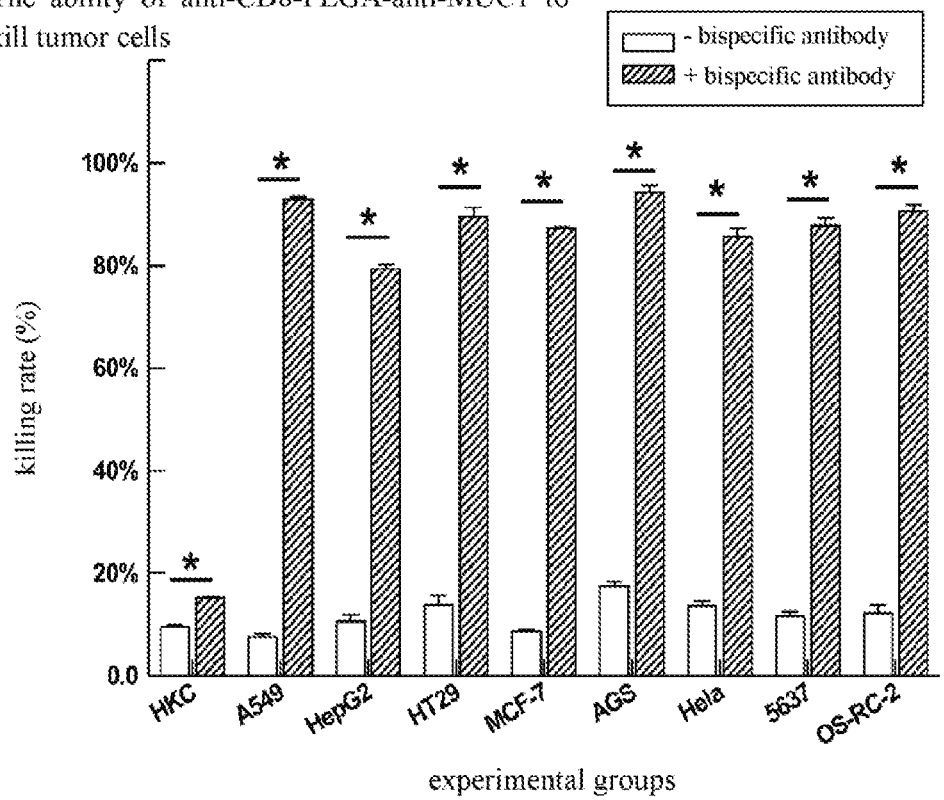
Figure 6:
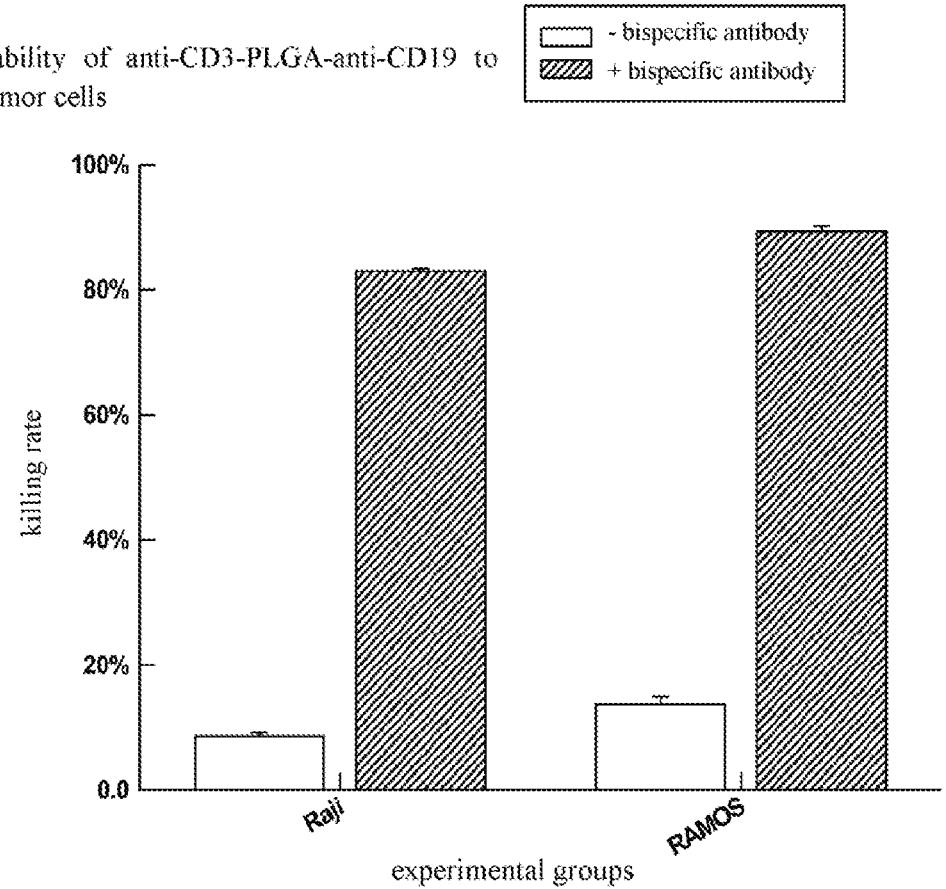
Figure 7:
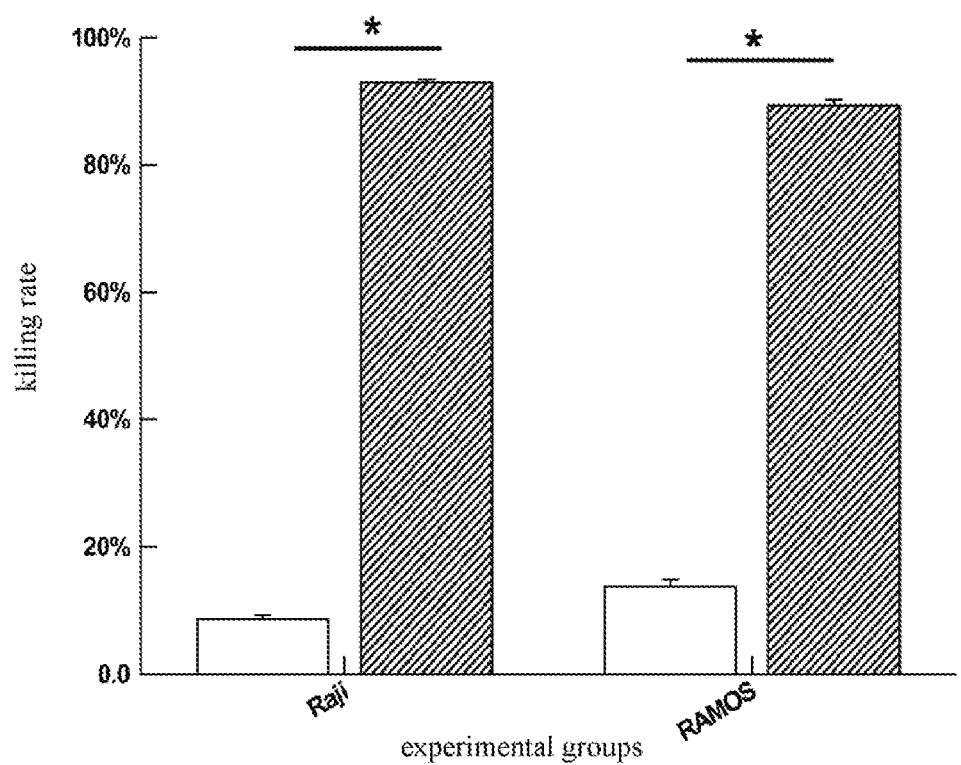
Figure 8:
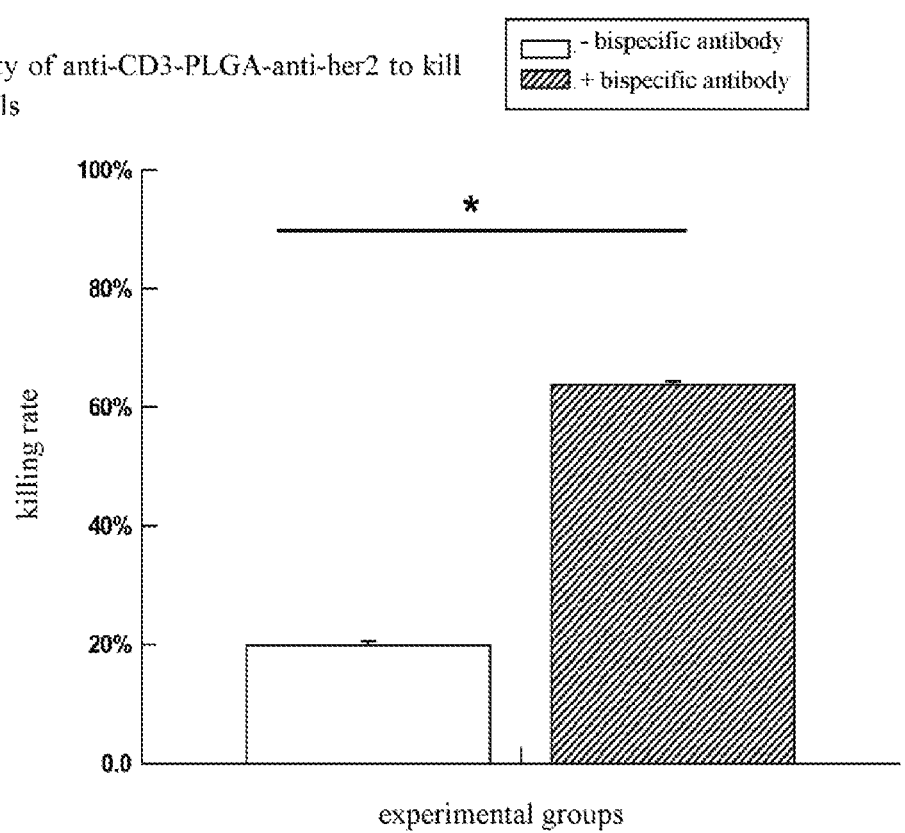
Figure 9:
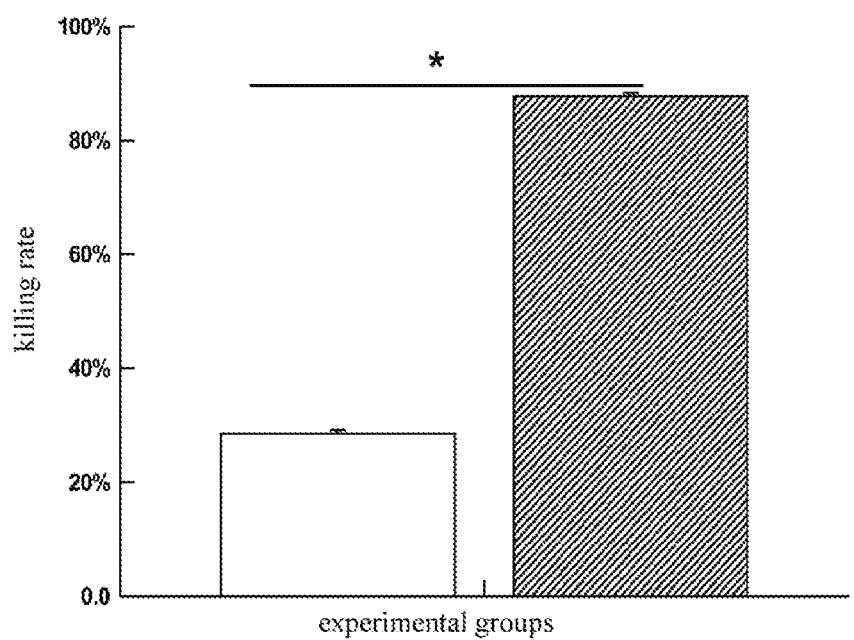

The results are shown in Table 3 and FIG. 5.

TABLE 3

The ability of anti-CD8-PLGA-anti-MUC1 to kill tumor cells

| Cancer cell | Killing rate | |
| --- | --- | --- |
| | Effect control group | Experimental group |
| HKC | 9.66% | 13.21% |
| A549 | 7.59% | 87.35% |
| HepG2 | 10.67% | 82.44% |
| HT29 | 13.84% | 91.27% |
| MCF-7 | 8.62% | 87.23% |
| AGS | 17.56% | 92.17% |
| Hela | 13.57% | 87.54% |
| 5637 | 11.64% | 82.51% |
| OS-RC-2 | 12.24% | 87.57% |

Note:
HKC - human embryo kidney epithelial cells;
A549 - human non-small cell lung cancer cells;
HepG2 - human liver cancer cells;
HT29 - human colon cancer cells;
AGS - human gastric adenocarcinoma cells;
Hela - human cervical cancer cells;
5637 human bladder cancer cells;
OS-RC-2 - human kidney cancer cells.

The bispecific antibodies anti-CD8-PLA-anti-MUC1 and anti-CD8-PCL-anti-MUC1 both showed a killing rate of more than 95% for human non-small cell lung cancer cells and human gastric adenocarcinoma cells; both showed a killing rate of more than 92% for human colon cancer cells and human kidney cancer cells; both showed a killing rate of nearly 90% for human breast cancer cells, human cervical cancer cells and human bladder cancer cells; showed a killing rate of about 80% for human liver cancer cells.

Example 7

Using the similar process as described above, other bispecific antibodies connected via nanoparticles, i.e. anti-CD3-PLGA-anti-CD19, anti-CD3-PLGA-anti-CD20, anti-CD3-PLGA-anti-her2 were prepared. The ability of the bispecific antibodies to kill tumor cells was evaluated. The results are shown in Tables 4-7 and FIGS. 6-9.

TABLE 4

The ability of anti-CD3-PLGA-anti-CD19 to kill tumor cells

| Cancer cell | Killing rate | |
| --- | --- | --- |
| | Effect control group | Experimental group |
| Raji | 8.59% | 82.91% |
| RAMOS | 13.67% | 89.36% |

Note:
Raji - black Burkitt lymphoma cells;
RAMOS - human B lymphocytoma cells.

TABLE 5

The ability of anti-CD3-PLGA-anti-CD20 to kill tumor cells

| Cancer cell | Killing rate | |
|---|---|---|
| | Effect control group | Experimental group |
| Raji | 8.59% | 92.71% |
| RAMOS | 13.67% | 88.27% |

Note:
Raji - black Burkitt lymphoma cells;
RAMOS - human B lymphocytoma cells.

TABLE 6

The ability of anti-CD3-PLGA-anti-her2 to kill tumor cells

| Cancer cell | Killing rate | |
|---|---|---|
| | Effect control group | Experimental group |
| MCF-7 | 19.88% | 63.84% |

Note:
MCF-7 - human breast cancer cells.

TABLE 7

The ability of anti-CD3-PLGA-anti-CD38 to kill tumor cells

| Cancer cell | Killing rate | |
|---|---|---|
| | Effect control group | Experimental group |
| Raji | 28.55% | 87.78% |

Note:
Raji - black Burkitt lymphoma cells.

Example 8. Anti-Tumor Experiment In Vivo

The anti-tumor effect of the bispecific antibodies of the present invention were evaluated. Specifically, healthy Balb-c nude mice (clean grade, female, four weeks old, 18-22 g in weight, purchased from the Guangdong Provincial Medicine Laboratory Animal Center) were inoculated with human lung adenocarcinoma cell A549 at armpit. After 3-4 weeks of inoculation, 30 nude mice with tumor diameter of about 0.5×0.5 cm were randomly divided into three groups for the experiment.

At the time of day 1, 3, 5, all mice were administered once via the tail-intravenous injection. 1×10$^6$ DC-CIK cells were injected each time in the DC-CIK group; 1×10$^6$ DC-CIK cells and 0.4 mg (a total amount of monoclonal antibody 0.4 µg) bispecific antibody anti-CD3-PLGA-anti-MUC1 were each time injected in the DC-CIK+bispecific antibody group; the same volume of saline was injected in the control group.

The tumor volume was recorded from the first day. Calculate the inhibitory rate of the bispecific antibodies against tumors.

After the death of all the animals in the control group and the DC-CIK alone treatment group, the experiment was terminated. The total time of observation was 128 days.

Figure 10:
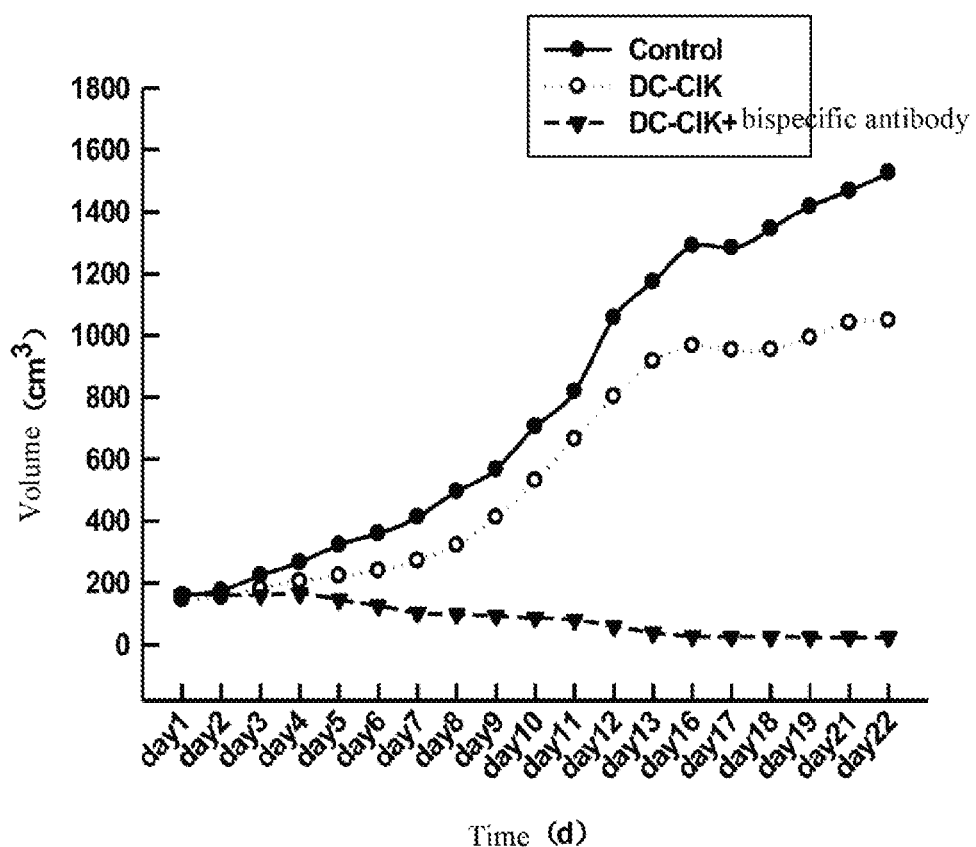
FIG. 10 shows the efficacy of a bispecific antibody anti-CD3-PLGA-anti-MUC1 on inhibiting tumor in vivo.

The average tumor volume of each group is shown in FIG. 10. The results showed that the inhibitory rate of the bispecific antibody anti-CD3-PLGA-anti-MUC1 against tumors was 88.73%, and the tumors of 60% of the animals (6/10) completely disappeared.

Figure 11:
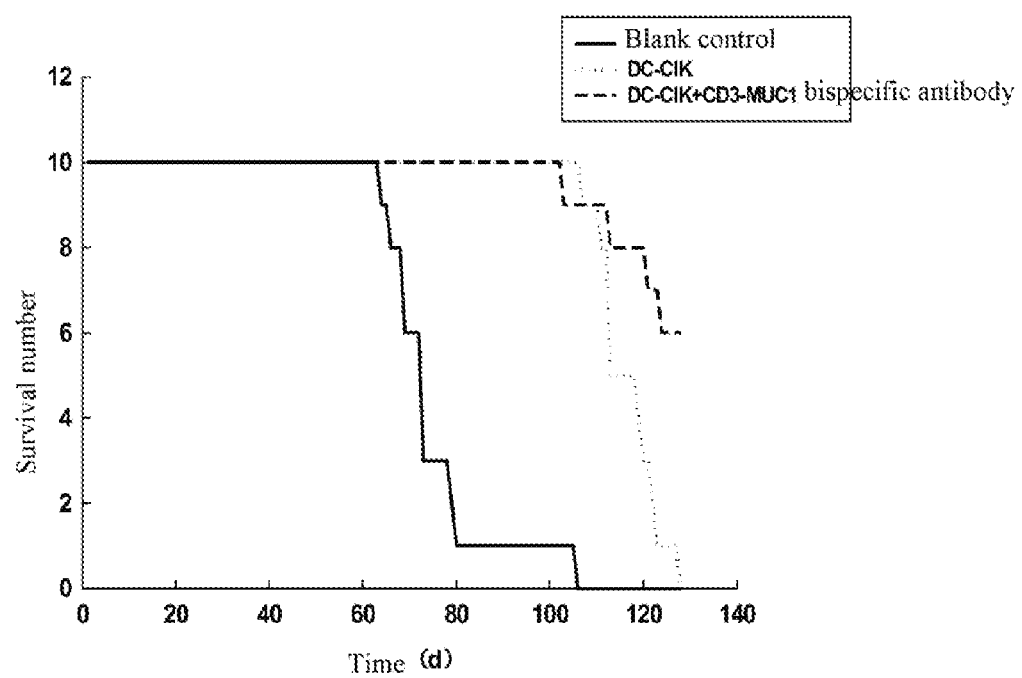
FIG. 11 shows the curve of laboratory animal mortality for antitumor experiments in vivo.

In terms of survival time, treatment with DC-CIK alone and treatment with DC-CIK+bispecific antibody both provided significant survival benefit when compared to untreated mice (FIG. 11). All the untreated mice died before day 105. All mice in the DC-CIK only treatment group died before day 128, while 6 mice still survived in the DC-CIK+ bispecific antibody treatment group.

As can be seen from the above Examples, the bispecific antibodies of the present invention have an improved ability to kill cancer cells by T cells, can be combined with the immune cells to enhance tumor killing ability, and have advantages such as less side effects, higher safety, lower cost, easy to use and so on as compared to CAR-T immune cell therapy.

The Applicant declares that the present invention illustrates the processes of the present invention via the above-described Examples, but the invention is not limited to the above-described process steps, i.e. it is not meant that the present invention must be carried out in accordance with the above-described process steps. It will be apparent to those skilled in the art that any improvements to the present invention, equivalents of the materials selected for use in the present invention, addition of auxiliary ingredients, selection of specific ways, etc., are within the disclosure and protection scope of the present invention without departing from the idea, spirit and scope of the invention.

We claim:

1. A bispecific antibody capable of being combined with an immune cell to enhance a targeting tumor killing capability, wherein the antibody comprises a first antibody moiety that binds to an antigen expressed on an effector T cell and a second antibody moiety that binds to an antigen expressed on a target cell, wherein the first antibody moiety and the second antibody moiety are connected by a nanomaterial which is a biodegradable nanomaterial, wherein the nanomaterial is polylactic acid-glycolic acid, the target cell is a cancer cell, the antigen expressed on the target cell is Muc1, and the antigen expressed on the effector T cell is CD3.

2. A method for producing a bispecific antibody according to claim 1, which comprises connecting the nanomaterial to the first antibody moiety and the second antibody moiety.

3. The method according to claim 2, which comprises the steps of: (1) preparation, collection and activation of the nanomaterial; (2) connecting the nanomaterial obtained in step (1) with a mixture of the first antibody moiety and the second antibody moiety.

4. The method according to claim 3, wherein the nanomaterial is polylactic acid-glycolic acid and the solvent is any one of acetone, butanone, methanol, ethanol or isopropanol or a mixture thereof.

5. A method of treating a tumor in a subject comprising administering to the subject a bispecific antibody according to claim 1.

6. The method according to claim 5, wherein the tumor is selected from the group consisting of liver cancer, non-small cell lung cancer, small cell lung cancer, adrenocortical carcinoma, acute (chronic B) lymphocytoma, myeloma, prostate cancer, breast cancer, esophageal cancer, gastric cancer, colorectal cancer, cervical cancer, kidney cancer, bladder cancer and lymphoma.

* * * * *